(12) United States Patent  
Blunn et al.

(10) Patent No.: US 8,628,584 B2
(45) Date of Patent: Jan. 14, 2014

(54) TRANSCUTANEOUS PROSTHESIS

(75) Inventors: Gordon Blunn, Royston (GB); Justin Cobb, London (GB); Allen Goodship, Wheathamstead (GB); Paul Unwin, Radlett (GB)

(73) Assignee: University College London, London (GB)

( * ) Notice: Subject to any disclaimer, the term of this patent is extended or adjusted under 35 U.S.C. 154(b) by 725 days.

(21) Appl. No.: 11/306,584

(22) Filed: Jan. 3, 2006

(65) Prior Publication Data

US 2007/0073412 A1    Mar. 29, 2007

Related U.S. Application Data

(63) Continuation of application No. 10/311,589, filed as application No. PCT/GB01/02771 on Jun. 22, 2001, now Pat. No. 7,014,661.

(30) Foreign Application Priority Data

Jun. 23, 2000   (GB) .................................. 0015479.9

(51) Int. Cl.
  *A61F 2/02*    (2006.01)
  *A61F 2/28*    (2006.01)
(52) U.S. Cl.
  USPC ..................................... 623/23.76; 623/23.57
(58) Field of Classification Search
  USPC ............ 623/11.11, 16.11, 23.48, 23.49, 23.5, 623/23.55, 23.56, 23.57, 23.76
  See application file for complete search history.

(56) References Cited

U.S. PATENT DOCUMENTS

| | | |
|---|---|---|
| 3,947,897 A | 4/1976 | Owens |
| 4,143,426 A | 3/1979 | Hall et al. |
| 4,158,895 A | 6/1979 | Reswick et al. |
| 4,330,891 A | 5/1982 | Branemark et al. |

(Continued)

FOREIGN PATENT DOCUMENTS

| | | |
|---|---|---|
| AU | 199657577 B2 | 1/1998 |
| DE | 3439993 A1 | 5/1986 |

(Continued)

OTHER PUBLICATIONS

Notice for Reasons for Rejection; Date of Dispatch Jul. 22, 2008, issued in corresponding Japanese Patent Application No. 2002-503196 with English translation.

(Continued)

*Primary Examiner* — William H. Matthews
(74) *Attorney, Agent, or Firm* — Buchanan Ingersoll & Rooney PC

(57) ABSTRACT

A transcutaneous prosthesis includes a first component shaped for implantation into a bone, the first component including flutes or grooves on a surface thereof for deterring rotation of the prosthesis within a bone; a second component adapted for location between the bone and the skin, the second component having a surface treatment for stimulation of fibroblastic cell proliferation and attachment of epithelial cells; and a third component adapted for location to extend from the skin surface and is adapted to extend directly from the skin surface in use, the third component having a coating of a non-stick material on an outer surface thereof, the coating having a surface energy that is lower than a surface energy of the first and second components and which is low enough to deter bacterial adhesion.

42 Claims, 3 Drawing Sheets

(56) References Cited

U.S. PATENT DOCUMENTS

| | | | |
|---|---|---|---|
| 4,549,319 A * | 10/1985 | Meyer | 623/23.23 |
| 5,026,397 A | 6/1991 | Aoki et al. | |
| 5,169,597 A | 12/1992 | Davidson et al. | |
| 5,336,268 A | 8/1994 | Rispeter | |
| 5,501,706 A | 3/1996 | Arenberg | |
| 5,578,086 A | 11/1996 | Prescott | |
| 5,709,683 A | 1/1998 | Bagby | |
| 5,723,038 A | 3/1998 | Scharnweber et al. | |
| 5,725,573 A | 3/1998 | Dearnaley et al. | |
| 5,981,827 A | 11/1999 | Devlin et al. | |
| 6,541,024 B1 | 4/2003 | Kadiyala et al. | |

FOREIGN PATENT DOCUMENTS

| | | |
|---|---|---|
| DE | 94 00 720.9 | 6/1995 |
| DE | 198 26 638 A1 | 12/1999 |
| EP | 0 545 542 A1 | 6/1993 |
| EP | 0 547 354 A1 | 6/1993 |
| EP | 0 806 212 A1 | 5/1997 |
| GB | 2 139 095 A | 11/1984 |
| JP | 62-204759 | 0/9198 |
| JP | 61-200903 | 9/1986 |
| JP | 4-183463 | 6/1992 |
| JP | 05-155730 | 6/1993 |
| RU | 2 114 579 C1 | 7/1998 |
| SU | 1454438 A1 | 1/1989 |
| WO | 89/04153 A1 | 5/1989 |
| WO | WO 97/02310 A1 | 1/1997 |
| WO | 97/46179 | 12/1997 |

OTHER PUBLICATIONS

International Search Report in PCT/GB 01/02771 dated Nov. 14, 2001.

Search Report Under Section 17 in Application No. GB 0115381.6 dated Nov. 29, 2001.

Search Report Under Section 17 in Application No. GB 0015479.9 dated Dec. 11, 2000.

Notice of Reasons for Rejection issued in corresponding JP Application No. 2002-503196 with English Language Translation, date of dispatch Mar. 3, 2009.

"Modulation of the Soft Tissue Reactions to Percutaneous Orthopaedic Implants", T.J. Smith et al., Wiley InterScience, Journal of Orthopaedic Research, Jul. 2006, pp. 1377-1383.

"Fibronectin silanized titanium alloy: a bioinductive and durable coating to enhance fibroblast attachment in vitro," C.A. Middleton, et al., Wiley InterScience, Wiley Periodicals, Inc., pp. 1032-1038 (Jun. 21, 2007).

"Development of a soft tissue seal around bone-anchored transcutaneous amputation prostheses", C.J Pendegrass et al., Science Direct, Biomaterials, pp. 4183-4191 (2006).

"Rehabilitation of the trans-femoral amputee with an osseointegrated prosthesis: the United Kingdom experience", J. Sullivan et al., Prosthetics and Orthortics International, 2003, 27, pp. 114-120.

Extract from 'High Performance Biomaterials: A Comprehensive Guide to Medical and Pharmaceutical Applications', Michael Szycher, 1st Edition (Oct. 1, 1991), CRC Press, pp. 213-215.

Applications and failure modes of percutaneous devices: A review, A. F. von Recum, Department of Interdisciplinary Studies, College of Engineering at Clemson University, Journal of Biomedical Materials Research, vol. 18, 1984, pp. 323-336.

"Molecular Basis of Bacterial Adhesion", T. Boland, et al., Handbook of Bacterial Adhesion; Principles, Methods, and Applications, Y.H An et al, Springer. pp. 29-41 (2000).

* cited by examiner

TRANSCUTANEOUS PROSTHESIS

CROSS REFERENCE TO RELATED APPLICATIONS

The present application is a continuation of U.S. application Ser. No. 10/311,589, filed on Apr. 28, 2003, which is a national stage filing of PCT/GB01/02771, filed on Jun. 22, 2001, which claims the priority of GB 0015479.9, which was filed on Jun. 23, 2000.

FIELD OF THE INVENTION

This invention relates to transcutaneous prosthesis and includes a method of fitting a prosthesis having a transcutaneous component to a patient.

BACKGROUND OF THE INVENTION

Amputation of limbs or digits can occur due to trauma or because of surgical removal. Examples of trauma include loss of fingers in machinery accidents, loss of limbs in car accidents or as a result of land mine explosions. Surgical removal can also be indicated as a result of cardio-vascular disease, diabetes and cancerous tumours to the bone or soft tissues.

After amputation, it is common to fit an external endo-prosthetic device that is attached to the body via by a skin interface. This commonly involves the manufacture of a custom-made socket which is secured to the stump using straps or clamps. A number of disadvantages arise from the use of such endo-prosthetic devices. For example:

(1) Skin is not a satisfactory high load bearing structure and often breaks down under load, becoming inflamed and uncomfortable and, in severe cases, pressure sores are formed which are difficult to heal.

(2) Changes in the shape of the stump may mean that a new custom-made socket is required.

(3) The use of sockets for receiving the stump are commonly sweaty and uncomfortable.

(4) Where a joint is involved, the external prosthesis is usually moved by muscle groups situated at a distance from the attached prosthesis and therefore motion is inefficient and unnatural.

OBJECTS AND SUMMARY

A major object of the present invention is to provide a prosthesis which overcomes some or all of the above disadvantages.

According to one aspect of the present invention there is provided a transcutaneous prosthesis which comprises a first component shaped for implantation into a bone, a second component intended for location between the bone and the skin, the second component having a surface treatment for stimulation of fibroblastic cell proliferation and attachment of epithelial cells and a third component intended for location exterior to the skin surface having a low surface energy which deters bacterial adhesion.

The prosthesis provided by the present invention is thus an intra-osseous transcutaneous prosthesis (ITAP) and has a number of advantages. For example, the first component is attached directly to load-bearing parts of the bony skeleton such that load is transmitted through bone. This means that the patient is able to apply much more power to the prosthesis. Also, motion and perception of movement is more natural because of the bone attachment. Moreover, because the skin takes no part in transmitting the load from the bone to the external part of the prosthesis, there is no pressure on the skin surface which would cause inflammation or discomfort.

The first component is formed with some suitable means for preventing rotation of the component in the bone which may comprise flutes or grooves or functionally similar shaped surfaces. These surfaces may be shaped to fit the profile of the intramedullary cavity, where present. Also, the first component is preferably provided with a surface treatment which encourages osseous integration. Suitable surface treatments include hydroxyapatite which is a hydrated calcium phosphate. The surface may also be formed with small apertures or pits to encourage integration between the bone and the first component. Where micro pits are formed in the surface, these may be of the order of 20 to 500 microns in size, preferably 20 to 100 microns.

The second component extends between the bone and the epithelial surface. This component is provided with a surface treatment for stimulating fibrous tissue ingrowth. Again, this component may be treated with an hydroxyapatite or aluminium oxide coating and the coating treated with materials which encourage the adhesion of epithelial cells to the second component. This component may also have a coating which is porous to encourage soft tissue ingrowth materials which encourage such growth include adhesion promoting proteins such as fibronectin or laminin. In order to aid adhesion of the fibrous tissue to the second component, the hypodermis is preferably surgically removed during the procedure of installing the prosthesis. The goal is to attach the skin to the implant to prevent movement of the skin and shear forces separating epithelial cells at the interface and underlying dermis and thereby permitting infection to enter between the skin and the prosthesis.

The third component comprises the exterior part of the prosthesis and this has a low surface energy which deters bacterial adhesion. A low surface energy can be achieved by coating this part of the prosthesis with a non-stick material such as a diamond-like carbon, a fluorinated polymer or a silicone polymer.

The prosthesis may be made up from separate components connected together, or two or more of the components may be formed integrally and given appropriate surface treatments.

The external component will preferably include a safety device comprising a linkage which breaks under an unusual load such as, for example, one caused by the patient falling. This will allow the external component to detach from the skeletal and transcutaneous component without causing damage to the bone or to the skin. An additional feature which will protect the fixation of an intramedullary post is an external device which limits torque transmitted to the adjustable fixation. The torque transmitted may be adjustable so that with time, the transmitted torque can be increased, as the internal component integrates with the bone.

In a further preferred embodiment of the present invention the second component may be provided so as to extend outwardly from the first and third components in a manner that increases the external surface area of the second component. The second component may also be provided with through holes which further increase the external surface area and allow growth of tissue through the second component. This has been found to advantageously facitate the integration of the component with fibrous tissue growth.

BRIEF DESCRIPTION OF THE DRAWINGS

The invention is illustrated by the accompanying drawings in which.

DETAILED DESCRIPTION OF THE PREFERRED EMBODIMENTS

Figure 1:
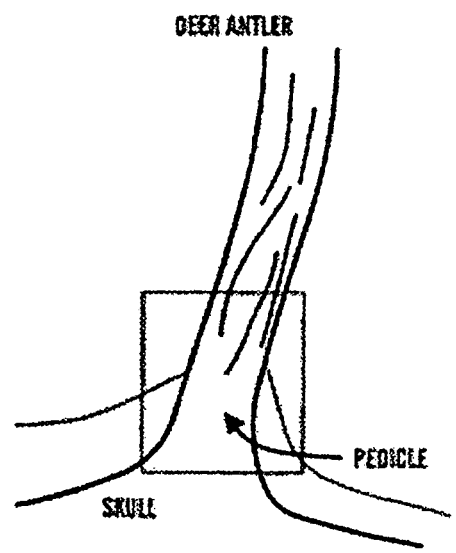
FIGS. 1 and 2 are diagrammatic views through part of a deer's antler and skull.
Figure 2:
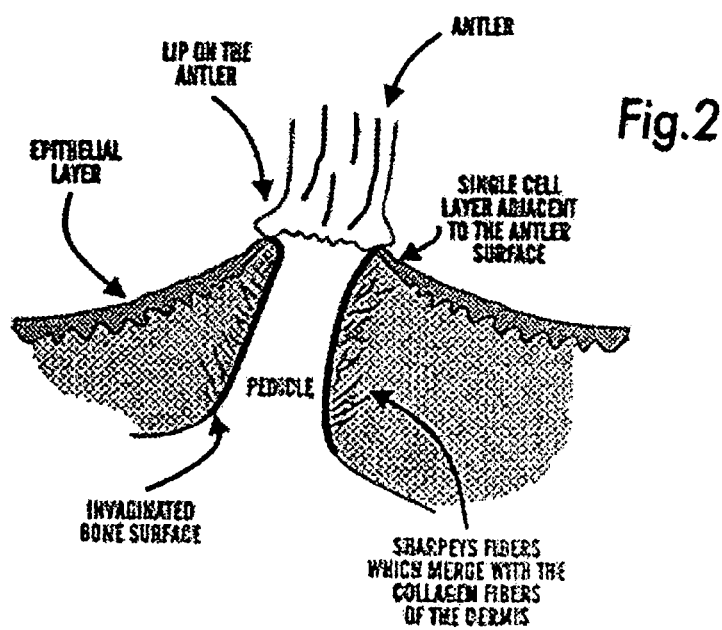

Referring to the drawings, the present invention was in part stimulated by study of the skin-bone interface around red deer antlers. This is a unique structure and may be thought of as a biological model for a transcutaneous implant. The deer antler at periods of the year is very heavily loaded during the rut. Histological examination indicates that the layer of skin epithelial cells become thinner as the epithelial layer approaches the antler, such that at the antler-skin interface an epithelial skin layer is only about one cell thick The dermis is intimately attached to the bone (pedicle) interface. The attachment is achieved through a series of "Sharpeys fibres" which attach to the dermis and to the bone and prevent differential skin movement. Antlers do not normally become infected and the bone structure is invaginated with small pores measuring 18 to 40 microns in diameter. This helps the interface between the dermis and the bone to resist shear stresses. These features are shown in FIGS. 1 and 2 of the accompanying drawings.

Figure 3:
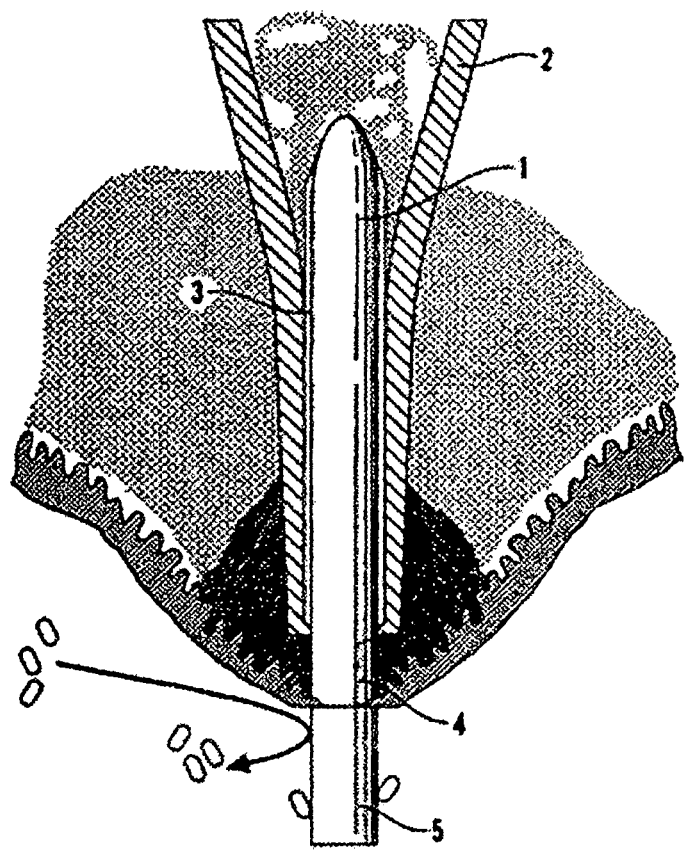
FIG. 3 is a diagrammatic part section showing a transcutaneous prosthesis in accordance with the invention, fitted to a patient.

The prosthesis of the present invention is shown in FIG. 3 and may be considered an artificial analogue of the deer's antler. The prosthesis comprises a first component (1) which is inserted into the intramedullary canal of a bone (2). Component (1) is formed with longitudinally extending cutting flutes which engage in the bone as the prosthesis is inserted into the intramedullary canal and resists rotation The surface of the component (1) may be coated with a material to encourage osseous integration such as a hydroxy apatite material and/or be micro-pitted. The second component (4) extends from the end of the bone to the surface of the skin. This component may be cylindrical as drawn, or could be flattened to a mushroom shape, thereby increasing the surface area over which the soft tissue can be attached. Component (4) is given a surface treatment to encourage attachment of the epithelial to the implant. Such surface treatments include giving the surface a micro-pitted structure and/or coating the surface with adhesion proteins such as laminin or fibronectin which encourage fibrous growth into the surface of the component (4) of the prosthesis.

Prior to installing the prosthesis, the hypodermis is preferably surgically removed. Further, a surface is provided on the second component which is porous and promotes fibrous tissue ingrowth. Suitable materials for coating the surface include alumina oxide ceramics and hydroxy apatite. This surface, preferably after being given a porous surface treatment, is coated with an adhesion promoting protein, e.g. by spraying the prosthesis with a solution of the adhesion-promoting protein, by dipping the prosthesis in a concentrated solution of the protein and freeze drying, or by dipping into a sterile solution of the adhesion-promoting protein prior to implantation The removal of the hypodermis surgically during the amputation and installation procedure assists in stimulating attachment of the skin to the implant and thereby prevents shear forces on the skin separating the epithelial cells at the interface.

The third component (5) of the prosthesis extends from the skin and is given a non-stick surface on its exterior portion Suitable materials include fluorinated polymers such as polytetrafluoroethylene, siliconised polymers and diamond like carbon. The presence of a non-stick surface discourages bacteria from attaching to the prosthesis and helps to prevent infection. The non-stick surface may be applied to the exterior portion of the third component (5) using the technique of chemical vapour deposition (CVD). The use of CVD is well known in the art for applying a surface of diamond-like carbon. When applying a surface layer of diamond, as disclosed in EP-B-0545 542 the method generally involves providing a mixture of hydrogen or oxygen gas and a suitable gaseous carbon compound such as a hydrocarbon, applying energy to that gas to dissociate the hydrogen into atomic hydrogen or the oxygen into atomic oxygen and the carbon into active carbon ions, atoms or CH radicals and allowing such active species to deposit on the substrate to form diamond. The energy to cause dissociation may be provided in a number of ways common to the art, for example by hot filament or by microwave source. A non-stick surface of fluorinated polymer or silicone polymer may be applied to the third component by polymerising a monomer or prepolymer in contact with the component.

It may be convenient to apply the low energy surface treatment to the third component while masking the remaining components of the prosthesis. Also, the second component of the prosthesis may be treated with the adhesion-promoting protein after applying the low energy surface to the third component, and it may be desirable to mask the third component while applying the adhesion-promoting protein.

The third component may be connected to an artificial limb or digit. For example, in the case of a replacement finger or part finger, the first component may be implanted into the remaining bone with the second component instituting the transcutaneous portion, and the third component extending beyond the severed stump. An artificial digit or part digit can then be attached to the third component.

The prosthesis may be implanted either in a one-stage procedure or in a two-stage procedure where the first component is implanted into the bone and allowed to integrate before the transcutaneous part is attached.

Figure 4:
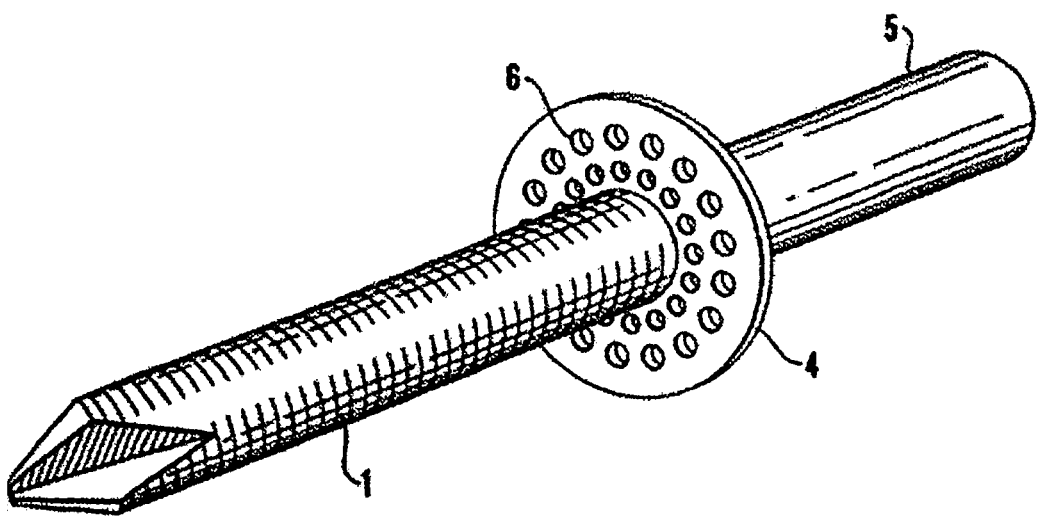
FIG. 4 is a perspective view of a preferred embodiment of a prosthesis in accordance with the present invention drawn on a larger scale compared with FIG. 3.

There is shown in FIG. 4 a further preferred embodiment of the present invention wherein the second component (4) is extended in an outward direction perpendicular to the first and third components in a plate like form. This feature provides the second component (4) with a large surface area which advantageously facilitates the integration of the second component (4) with fibrous tissue growth. As also shown in FIG. 4, through holes (6) may be provided in the plate like extension of the second component (4), which further increase the external surface area and also allowing tissue to grow through the second component further facilitating integration. Although the above description refers to a series of components, it will be appreciated that each component may be a portion of an integral element manufactured from a single piece of material. It is, however, preferred that a frangible linkage is provided between the third and second components or between the second and first component, so that in the event that a high load is applied to the third component, or to a member attached thereto, the linkage will fair so as to protect the implanted bone from injury.

While the present invention has been described with particular reference to the provision of a prosthesis for replacement of lost digits or limbs, the invention is also applicable to other prosthesis which extend through the skin, e.g. dental implants.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A transcutaneous prosthesis which comprises:
   a first component shaped for implantation into a bone;
   a second component adapted for location between the bone and the skin, the second component having an outer surface having one or more surface treatments for stimulation of fibroblastic cell proliferation and attachment of epithelial cells, the surface treatments being porous, being micro-pitted, and/or being coated with an external coating of a material selected from hydrated calcium phosphate, adhesion promoting proteins and alumina oxide ceramics; and
   a third component adapted for location to extend directly from the skin surface in use, the third component having an outer surface thereof, wherein the outer surface of the third component comprises a non-stick material whereby the surface has a surface energy that is lower than a surface energy of the first and second components and which deters bacterial adhesion,
   wherein, in use, a transition from the second component to the third component is essentially at the surface of the skin and the third component extends from the skin surface, such that the non-stick outer surface of the third component is adjacent to the surface treated outer surface of the second component when the first component is implanted in a bone.

2. A prosthesis according to claim 1 wherein the components are integrally formed and have different surface treatments.

3. A prosthesis according to claim 1, wherein the first component has a surface treatment which stimulates bone growth and osseous integration.

4. A prosthesis according to claim 1, wherein the second component has a micro-pitted surface.

5. A prosthesis according to claim 1, wherein the surface of the second component carries a protein coating.

6. A prosthesis according to claim 1, wherein the second component extends outwardly from the first and third components.

7. A prosthesis according to claim 6, wherein the second component has through-holes.

8. A prosthesis according to claim 1, where the third component carries a coating comprising a fluoro- or silicone polymer.

9. A prosthesis according to claim 1, wherein the third component carries a coating comprising diamond like carbon.

10. A prosthesis according to claim 1, wherein the third component includes a frangible or detachable linkage which permits an external component to detach in the event that an unusually high load is applied to the prosthesis.

11. A prosthesis according to claim 1, in which the third component is adapted for connection to an artificial limb or digit.

12. A prosthesis according to claim 5, wherein the protein coating is fibronectin or laminin.

13. A prosthesis according to claim 1, wherein the surface of the second component carries a hydrated calcium phosphate coating.

14. A prosthesis as claimed in claim 13, wherein the hydrated calcium phosphate coating is a coating of hydroxy apatite.

15. A prosthesis as claimed in claim 1, wherein the surface energy of the third component is a surface energy level of a non-stick material comprising a fluoro or silicone polymer or diamond-like carbon.

16. A transcutaneous prosthesis which comprises:
    a first component shaped for implantation into a bone, the first component including means on a surface thereof for deterring rotation of the prosthesis within a bone;
    a second component adapted for location between the bone and the skin, the second component having a surface treatment for stimulation of fibroblastic cell proliferation and attachment of epithelial cells; and
    a third component adapted for location to extend from the skin surface and adapted to extend directly from the skin surface in use, wherein the second component is located between the first and third components in use, the third component having a coating of a non-stick material on an outer surface thereof, the coating having a surface energy that is lower than a surface energy of the first and second components so as to deter bacterial adhesion on the third component.

17. A prosthesis according to claim 16, wherein the components are integrally formed and have different surface treatments.

18. A prosthesis according to claim 16, wherein the second component has a micro-pitted surface.

19. A prosthesis according to claim 16, where the non-stick coating of the third component comprises a fluoro- or silicone polymer.

20. A prosthesis according to claim 16, where the non-stick coating of the third component comprises diamond like carbon.

21. A prosthesis according to claim 16, wherein the surface of the second component carries a protein coating.

22. A prosthesis according to claim 16, wherein the surface of the second component carries a hydrated calcium phosphate coating.

23. A transcutaneous prosthesis which comprises:
    a first component shaped for implantation into a bone,
    a second component adapted for location between the bone and the skin, the second component having a surface treatment for stimulation of fibroblastic cell proliferation and attachment of epithelial cells, and
    a third component adapted for location to extend from the skin surface and adapted to extend directly from the skin surface, in use, wherein the second component is located between the first and third components in use, wherein an outer surface of the third component comprises a non-stick material, whereby the outer surface of the third component has a surface energy that is lower than a surface energy of the first and second components and which deters bacterial adhesion,
    wherein a distance between the first component and the third component is such that a transition from the second component to the third component is essentially at the surface of the skin and the third component extends from the skin surface when the first component is implanted in a bone.

24. A prosthesis according to claim 23, wherein the components are integrally formed and have different surface treatments.

25. A prosthesis according to claim 23, wherein the second component has a micro-pitted surface.

26. A prosthesis according to claim 23, where the non-stick coating of the third component comprises a fluoro- or silicone polymer.

27. A prosthesis according to claim 23, where the non-stick coating of the third component comprises diamond like carbon.

28. A prosthesis according to claim 23, wherein the surface of the second component carries a protein coating.

29. A prosthesis according to claim 23, wherein the surface of the second component carries a hydrated calcium phosphate coating.

30. A transcutaneous prosthesis which comprises:
a first component shaped for implantation into a bone,
a second component adapted for location between the bone and the skin, the second component having a surface treatment for stimulation of fibroblastic cell proliferation and attachment of epithelial cells, and
a third component adapted for location to extend from the skin surface and adapted to extend directly from the skin surface, in use,
wherein the second component is located between the first and third components in use, the third component having an outer surface,
wherein the outer surface of the third component has a non-stick coating material whereby it has a surface energy that is lower than a surface energy of the first and second components and which deters bacterial adhesion,
wherein a distance between the first component and the third component is such that a transition from the second component to the third component is essentially at the surface of the skin and the third component extends from the skin surface when the first component is implanted in a bone.

31. A prosthesis according to claim 30, wherein the components are integrally formed and have different surface treatments.

32. A prosthesis according to claim 30, wherein the second component has a micro-pitted surface.

33. A prosthesis according to claim 30, where the non-stick coating of the third component comprises a fluoro- or silicone polymer.

34. A prosthesis according to claim 30, where the non-stick coating of the third component comprises diamond like carbon.

35. A prosthesis according to claim 30, wherein the surface of the second component carries a protein coating.

36. A prosthesis according to claim 30, wherein the surface of the second component carries a hydrated calcium phosphate coating.

37. A prosthesis according to claim 6, wherein the second component extends in an outward direction perpendicular to the first and third components, said second component thereby defining a substantially planar surface.

38. A prosthesis according to claim 37, wherein the second component has through holes, each through hole defining an opening in the substantially planar surface of the second component.

39. A prosthesis according to claim 6, wherein the second component is mushroom shaped.

40. A transcutaneous prosthesis for implantation with a bone and skin, comprising:
a first component for implanting into the bone;
a second component for implanting between the bone and the skin, the second component including an outer surface having one or more surface treatments for stimulation of fibroblastic cell proliferation and attachment of epithelial cells; and
a third component for extending directly from the skin in use, the third component having an outer surface comprising of a non-stick material, wherein the outer surface has a surface energy which is low enough to deter bacterial adhesion,
wherein, in use, the first component is implanted such that a transition from the second component to the third component is essentially at the surface of the skin and the third component extends from the skin surface when the first component is implanted in the bone, such that the non-stick outer surface of the third component is adjacent to the surface treated outer surface of the second component.

41. A transcutaneous prosthesis adapted for surgical attachment to bone and skin, comprising:
a first component implanted into a bone;
a second component positioned between the bone and the skin, the second component including an outer surface having one or more surface treatments for stimulation of fibroblastic cell proliferation and attachment of epithelial cells; and
a third component extending directly from the skin in use, the third component having an outer surface comprising of a non-stick material, wherein the outer surface has a surface energy which deters bacterial adhesion,
the second component is positioned between the first component and the third component in use, such that the non-stick outer surface of the third component is adjacent to the surface treated outer surface of the second component, and
wherein, in use, the first component is implanted in a bone such that a transition from the second component to the third component is essentially at the surface of the skin and the third component extends from the skin surface.

42. A transcutaneous prosthesis comprising:
a first component shaped for implantation into a bone,
a second component adapted for location between the bone and the skin, the second component having a surface treatment for stimulation of fibroblastic cell proliferation and attachment of epithelial cells, and
a third component adapted for location to extend directly from the skin surface in use, the third component having an outer surface thereof, wherein the outer surface of the third component comprises a non-stick material whereby the surface has a low surface energy that is lower than a surface energy of the first and second components and which deters bacterial adhesion,
the second component being located between the first component and the third component in use, such that the non-stick outer surface of the third component is adjacent to the surface treated outer surface of the third component.

* * * * *